United States Patent
Kraeutle

[11] 3,958,176
[45] May 18, 1976

[54] METHOD FOR MEASURING SUITABILITY OF ALUMINUM FOR USE IN CERTAIN PROPELLANTS

[75] Inventor: Karl J. Kraeutle, China Lake, Calif.

[73] Assignee: The United States of America as represented by the Secretary of the Navy, Washington, D.C.

[22] Filed: Feb. 24, 1975

[21] Appl. No.: 552,504

[52] U.S. Cl. .............................. 324/65 R; 73/15 R; 73/35
[51] Int. Cl.² ....................................... G01R 27/02
[58] Field of Search .......... 324/65 R; 73/15 R, 15.4, 73/35; 23/253 R

[56] References Cited
UNITED STATES PATENTS

| | | | |
|---|---|---|---|
| 3,222,916 | 12/1965 | Davis | 73/15 R |
| 3,303,690 | 2/1967 | Meers, Jr. | 73/35 |
| 3,578,756 | 5/1971 | Evans et al. | 73/15 R |
| 3,580,049 | 5/1971 | Cardwell et al. | 73/35 |
| 3,701,278 | 10/1972 | Askins et al. | 73/35 |
| 3,899,919 | 8/1975 | Geisler et al. | 73/35 |

OTHER PUBLICATIONS

Crawford, Jr. et al., Direct Determination of Burning Rates of Propellant Powders, Analytical Chemistry, Feb. 1947, pp. 630–633.
Spenadel, Burning Rate Measurement of Solid Propellants, The Review of Scientific Instruments, July 1961, pp. 837–839.

Primary Examiner—Stanley T. Krawczewicz
Attorney, Agent, or Firm—R. S. Sciascia; Roy Miller; Lloyd E. K. Pohl

[57] ABSTRACT

The resistance of aluminum particles which contain aluminum oxide coatings is measured while the particles are being slowly heated. The resistance is plotted against temperature. If the resistance drops off to zero before the temperature reaches 660°C, the particles are undesirable for use as a fuel in certain rocket propellants.

3 Claims, 4 Drawing Figures

12 = SAMPLE TUBE
13 = REFERENCE TUBE FOR TEMPERATURE MEASUREMENT
14 = FEEDBACK THERMOCOUPLE (CHROMEL/ALUMEL)
15 = OHMMETER
16 = PLOTTER
17 = AMPLIFIER
18 = PROGRAMMER
19 = CONTROLLER

RECORDER
R = f(T, t)
T = f(t)
X = f(t)
R = ELECTRICAL RESISTANCE
T = TEMPERATURE
t = TIME

METHOD FOR MEASURING SUITABILITY OF ALUMINUM FOR USE IN CERTAIN PROPELLANTS

BACKGROUND OF THE INVENTION

1. Field of the Invention.

This invention relates to an electronic method for determining whether or not aluminum particles are suitable for use as a rocket propellant fuel.

2. Description of the Prior Art.

The use of aluminum particles as a fuel in solid rocket propellants is, of course, well known. It is also well known that aluminum powder is not really aluminum but rather aluminum coated with aluminum oxide.

Aluminum powder, i.e., aluminum particles coated with aluminum oxide, comes to those who manufacture solid rocket propellants from several different sources. Perhaps because each source has at least some unique techniques which it uses in the manufacture of aluminum powder, i.e., techniques which are different than those used by any other company, aluminum powder varies from source to source. More specifically, properties of the aluminum oxide coatings on aluminum particles vary depending on the source. Aluminum particles and, more specifically, the oxide coatings thereon even may vary from batch to batch when they are obtained from a single source.

High speed photography has recently shown that the oxide coatings on aluminum particles have much to do with how effective aluminum particles are insofar as their fuel qualities in a solid propellant are concerned. When as-purchased aluminum particles are used, they tend to agglomerate when heated. Agglomeration is undesirable. Accordingly, a method was developed for treating aluminum particles to render the coatings of oxide thereon more uniform and to heal the coatings, i.e., heal any flaws or scratches in the coatings where pure aluminum might be "peeking" through. The method involves strengthening the aluminum oxide coatings by baking the particles for from 10 to 35 hours at 560°C under 1 atmosphere of oxygen. High speed photography of burning rocket propellant grains has indicated that this process is very effective in reducing agglomeration.

In order to determine how long one should bake aluminum particles in the above-described process, for example, 10, 11, 12, . . . , 35 hours, it is necessary to test the particles. This could be done, of course, by baking small batches for 10, 11, 12, . . . , 35 hours, incorporating the batches into separate solid rocket propellant grains, burning the grains and observing the results with high speed photographic equipment. This would, however, obviously be a long, drawn out testing process. It is, accordingly, the primary objective of this invention to provide a simple, fast and effective method for testing powdered aluminum to determine whether or not it is suitable for use as a rocket propellant fuel.

SUMMARY OF THE INVENTION

According to this invention, the resistance of powdered aluminum is monitored while the powder is being slowly heated. The resistance is then plotted against temperature. If the resistance drops off to a rather small value before the temperature of the powder reaches 660°C, the powder is undesirable for use as a rocket propellant fuel. If, on the other hand, the resistance drops off to low values after the powder has been heated to 660°C, the powder is desirable for use as a rocket propellant fuel. The temperature of 660°C is important because at this point the aluminum liquifies and can agglomerate under certain circumstances.

DESCRIPTION OF THE PREFERRED EMBODIMENT

Figure 1:
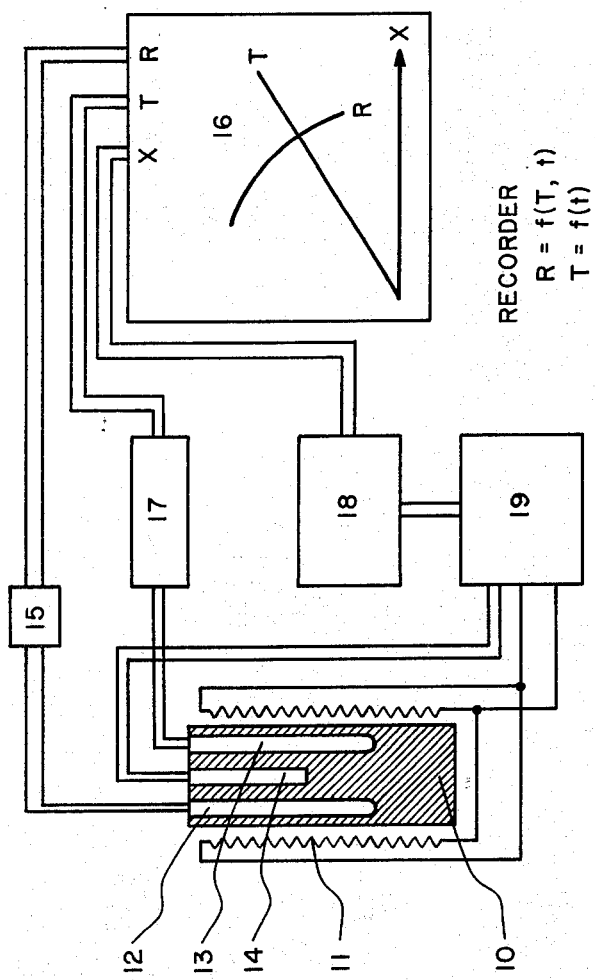
FIG. 1 shows the arrangement of components which are used to monitor the electrical resistance of aluminum powder according to this invention.

The resistance of aluminum powder (aluminum particles covered with aluminum oxide coatings) may be measured with an arrangement such as that depicted in FIG. 1. In FIG. 1 the numeral 10 is used to indicate a metal block which is heated by a wire wound furnace 11. The block 10 contains three bores 12, 13 and 14. Bore 12 contains a sample tube (not shown in FIG. 1) with an aluminum sample (not shown in FIG. 1) the resistance R of which is measured by an ohmmeter 15 and plotted as a function of time on plotter 16. Bore 13 contains a thermocouple (not shown in FIG. 1) to measure the temperature T. The electromotive force of the thermocouple in bore 13 is amplified with an amplifier 17 and then recorded on plotter 16 as a function of time. A programmer 18 and controller 19 are used to heat the furnace 11 at a constant rate. This is accomplished by a thermocouple (not shown in FIG. 1) in bore 14 which supplies a feedback signal to the controller 19 where it is compared with the signal of programmer 18. The difference between the two signals is used by the controller 19 to monitor the power input to the furnace 11 to obtain the heating rate as programmed in programmer 18. The heating rate is constant and has a value between 20° and 25°C per minute. The programmer 18 also sweeps the x-axis of plotter 16 at a constant rate and thus provides the time basis for heating rate measurement (slope of T versus X on plotter 16).

Figure 2:
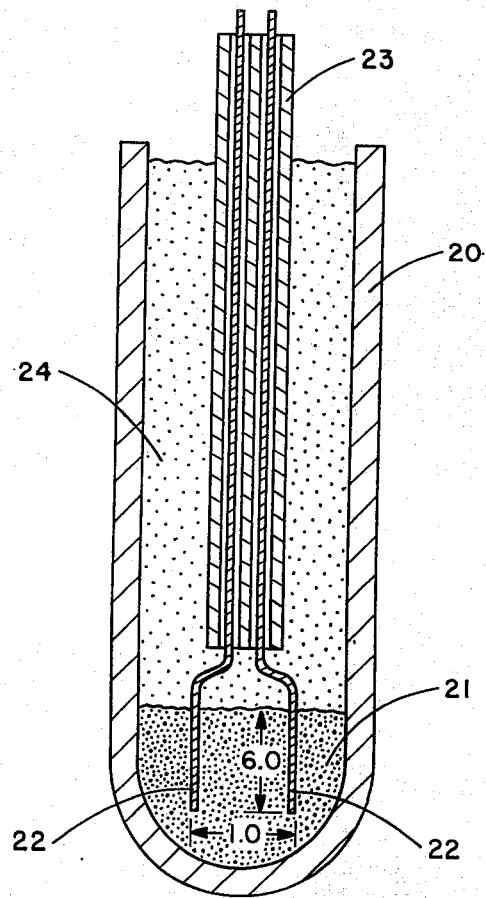
FIG. 2 depicts the sample tube.

FIG. 2 depicts in detail, the apparatus which is utilized in bore 12 of FIG. 1. The numeral 20 is used to indicate a quartz tube which holds the aluminum powder 21. Inserted into the aluminum powder are two platinum wires 22 which lead to the ohmmeter 15 of FIG. 1. The wires 22 are encased in an insulating tube 23 of recrystallized alumina with two bores. The aluminum powder 21 is covered with a layer of aluminum oxide powder 24. The aluminum oxide tube is fixed in the quartz tube by the aluminum oxide powder 24.

Figure 3:
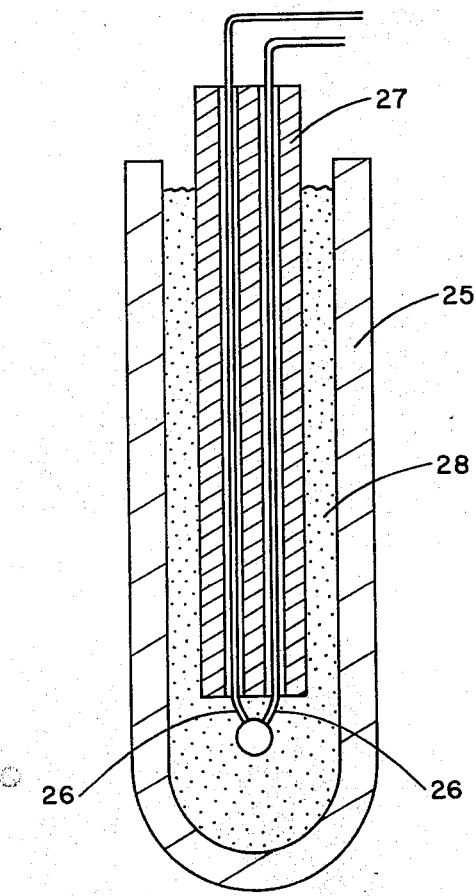
FIG. 3 shows the tube which contains the thermocouple for temperature measurement.

FIG. 3 depicts in detail the apparatus which is utilized in bore 13 of FIG. 1 to measure the temperature T. A quartz tube 25 contains two thermocouple wires 26. The wires 26 are insulated by a tube 27 of recrystallized alumina which contains two bores. The tube 27 is fixed in tube 25 by ignited aluminum powder 28.

Into bore 14 of FIG. 1 is inserted a thermocouple which consists of two wires which are insulated by an insulating tube similar to insulating tube 23 of FIG. 2 or 27 of FIG. 3.

Figure 4:
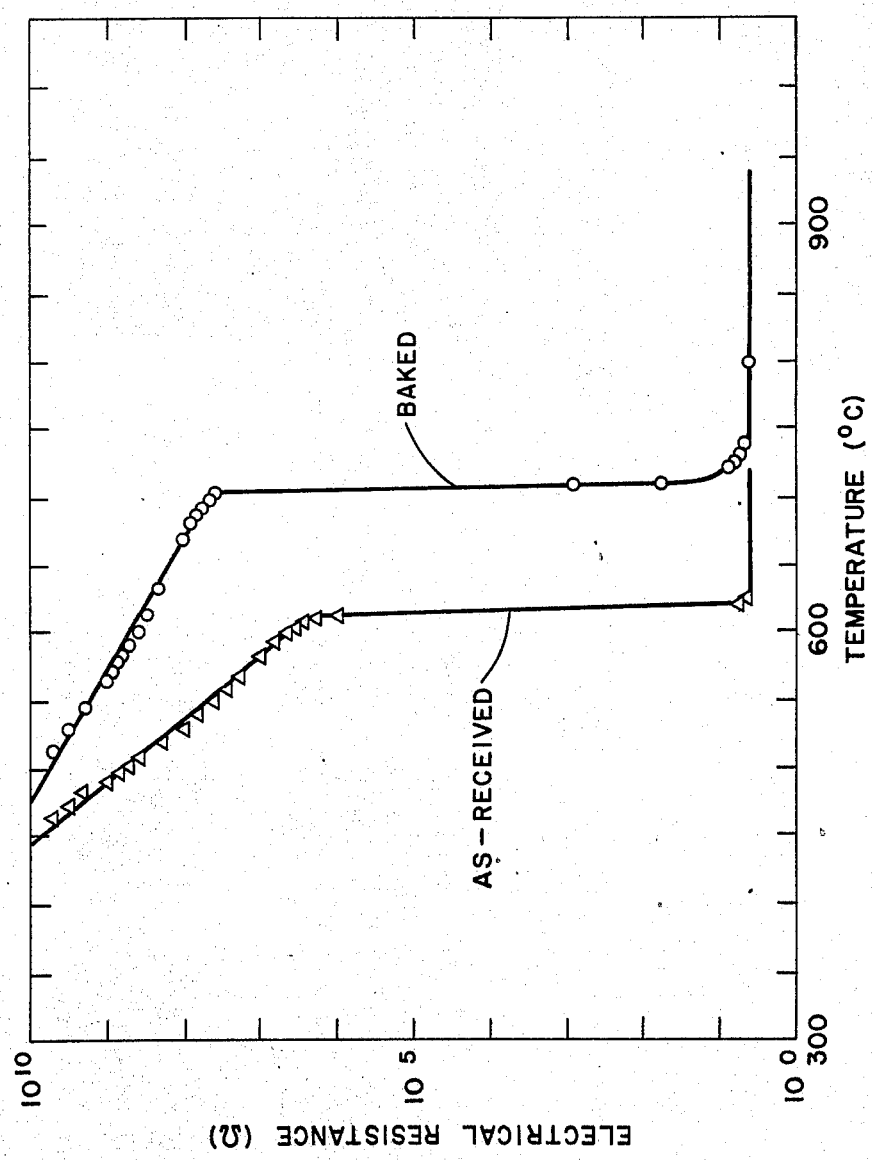
FIG. 4 illustrates typical curves produced when the resistance is plotted against temperature for as received and treated aluminum powder.

To carry out the process of this invention, one heats the aluminum powder (in the device of FIG. 2) at a controlled rate and measures the resistance of the powder as a function of temperature. FIG. 4 depicts typical curves obtained when one plots resistance R against temperature T for an undesirable powder, i.e., an as received one which high speed photography has shown to tend to agglomerate when incorporated into a solid rocket propellant and burned, and for a powder which has been baked in oxygen for 10 to 35 hours at 560°C. It will be noted from FIG. 4 that the resistance of the undesirable (as-received) powder drops off to a low value before a temperature of 660°C (the melting point of aluminum) is reached. It will also be noted that the baked powder curve of FIG. 4 is similar in shape to that of the as-received powder but that the resistance drops to a low value only after a temperature well above the melting point of 660°C is reached.

Numerous comparison tests in which the resistance of aluminum powder was plotted as a function of temperature prior to incorporating the powder into solid propellant formulations, burning it and recording the results with high speed photography have shown that one can reliably predict whether or not aluminum particles will tend heavily toward agglomeration or not, when burned, by noting whether or not the resistance drops to low values before or after reaching 660°C when the powder is heated. In the tests, a controlled heating rate of from about 20° to about 25°C per minute was used by utilizing the apparatus of FIGS. 1, 2 and 3 while the resistance was being measured. Typical resistance at the beginning of the heating cycle was about 5000 megohms.

To confirm the high speed photography results, combustion residues were collected and examined. Residue particles obtained from propellants which contained as-received aluminum powder were appreciably larger than those obtained from propellants which contained baked powder.

One may take the term "low values" used herein to mean values between about 5 and 10 ohms. The temperature of the resistance breakdown according to FIG. 4 indicates the transition from the high resistance of an insulator with a negative temperature coefficient of resistance to the low resistance of a metallic conductor, i.e., here aluminum, with a positive temperature coefficient of resistance.

What is claimed is:

1. A method for determining whether or not aluminum powder is desirable for use as a fuel in a rocket propellant comprising the steps of:
    a. simultaneously heating the powder at a controlled rate and monitoring the resistance and temperature of the powder; and
    b. determining whether or not the resistance of the powder approaches a low value before or after the powder has been heated to a temperature of 660°C.

2. The method according to claim 1 wherein the powder is heated at a rate of from about 20° to about 25°C per minute.

3. The method according to claim 2 wherein said low value is between about 5 to 10 ohms.

* * * * *